(12) United States Patent
Afriat et al.

(10) Patent No.: US 6,203,576 B1
(45) Date of Patent: Mar. 20, 2001

(54) COMPLETE KNEE JOINT PROSTHESIS

(75) Inventors: Jacques Afriat, Narbonne; Henri Audouy, Escalquens; Marc Nottebaert, Pont de L'Arn, all of (FR)

(73) Assignee: Groupe Controle Dedienne GCD Societe de Droit Francais, Clamart (FR)

( * ) Notice: Subject to any disclaimer, the term of this patent is extended or adjusted under 35 U.S.C. 154(b) by 0 days.

(21) Appl. No.: 09/319,113

(22) PCT Filed: Dec. 9, 1996

(86) PCT No.: PCT/FR96/01962

§ 371 Date: Sep. 1, 1999

§ 102(e) Date: Sep. 1, 1999

(87) PCT Pub. No.: WO98/25550

PCT Pub. Date: Jun. 18, 1998

(51) Int. Cl.[7] .......................................................... A61F 2/38
(52) U.S. Cl. ..................................... 623/20.27; 623/20.18; 623/20.26
(58) Field of Search .................................. 623/16, 18, 20, 623/23, 20.11–20.35, 20.27, 20.18, 20.26, 20.21, 20.28, 20.29, 20.3, 20.31, 16.11, 18.11

(56) References Cited

U.S. PATENT DOCUMENTS

| | | | |
|---|---|---|---|
| 4,353,135 | * 10/1982 | Forte et al. ................................ | 623/20 |
| 4,634,444 | * 1/1987 | Noiles ................................ | 623/20.27 |
| 4,888,021 | * 12/1989 | Forte et al. ........................ | 623/20.18 |
| 4,950,298 | * 8/1990 | Gustilo et al. ..................... | 623/20.15 |
| 5,011,496 | * 4/1991 | Forte et al. ........................ | 623/20.18 |
| 5,330,534 | 7/1994 | Herrington et al. . | |
| 5,358,527 | * 10/1994 | Forte ................................. | 623/20.27 |
| 5,997,577 | * 12/1999 | Herrington et al. .............. | 623/20.15 |

FOREIGN PATENT DOCUMENTS

| | | |
|---|---|---|
| 0 186 471 A2 | 7/1986 | (EP) . |
| 0 627 203 A2 | 12/1994 | (EP) . |
| 0 636 353 A1 | 2/1995 | (EP) . |
| 2685632 A1 | 7/1993 | (FR) . |
| 2021419 | 12/1979 | (GB) . |
| 95/25484 | 9/1995 | (WO) . |

* cited by examiner

Primary Examiner—Pedro Philogene
(74) Attorney, Agent, or Firm—Oliff & Berridge, PLC

(57) ABSTRACT

A complete knee joint prosthesis having prosthetic condyles as a part of the femoral element, wherein the prosthetic condyles have a curvature in the shape of a circular arc in their rear part, and the femoral element has, between these prosthetic condyles, a convex cylindrical wall with an axis that coincides with the axis of the circle in which the rear parts of the prosthetic condyles lie. Glenoid cavities of an intermediate plate have corresponding rear parts in the shape of a circular arc and a corresponding concave bearing surface in the shape of a circular arc for pivotably receiving the prosthetic condyles. The tibial element has a cylindrical pin and the intermediate plate comprises a cavity which receives this pin to provide the possibility of multidirectional movement of the prosthetic knee joint.

16 Claims, 2 Drawing Sheets

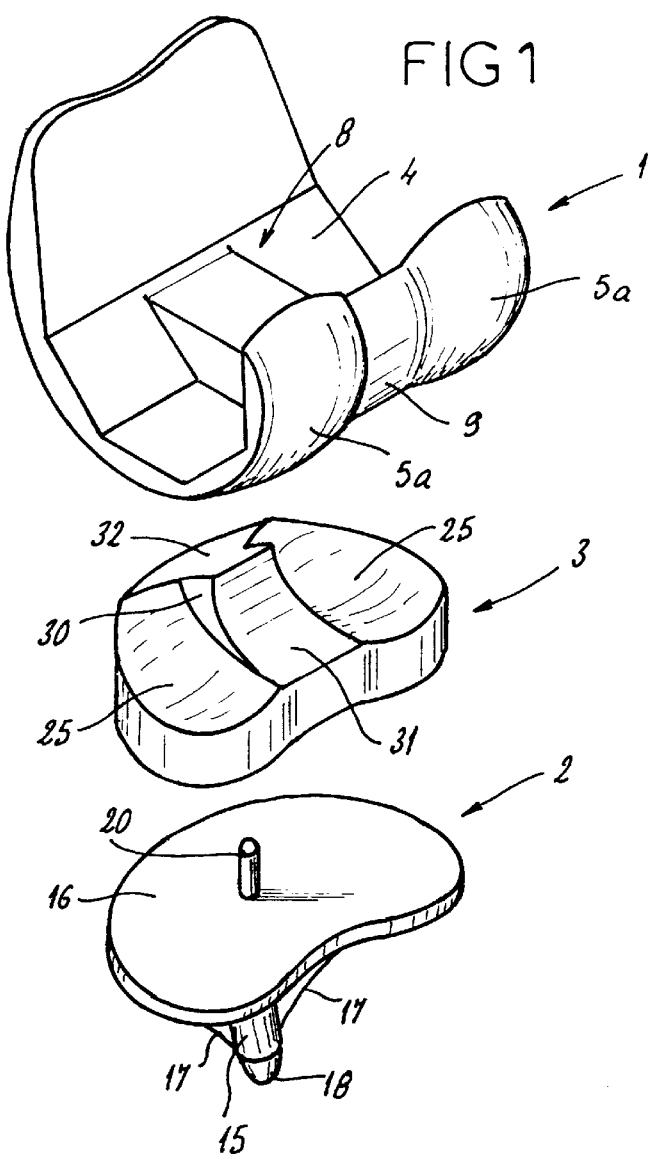
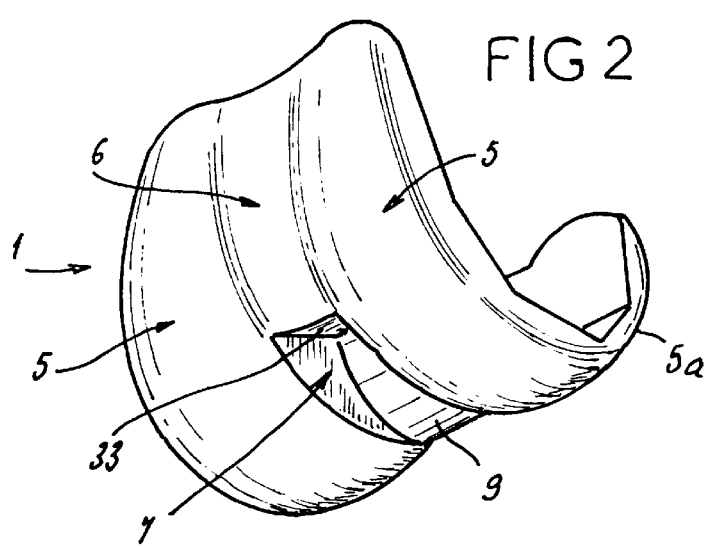

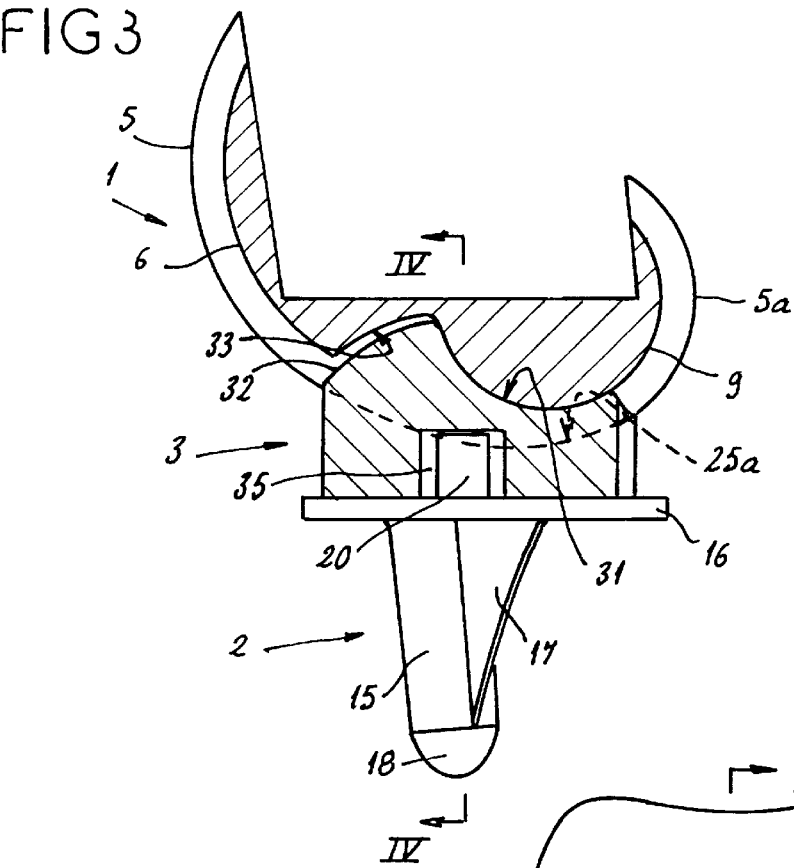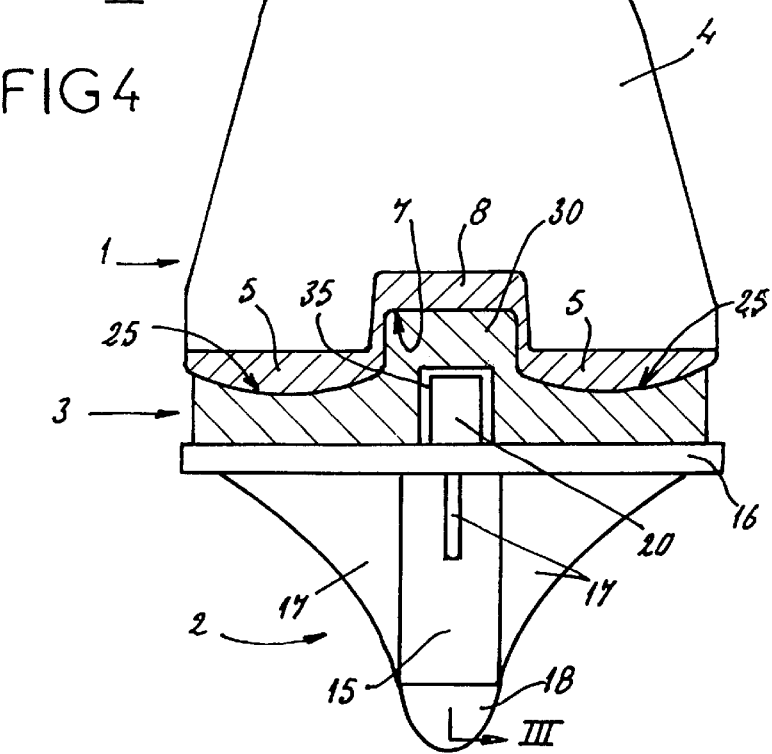

COMPLETE KNEE JOINT PROSTHESIS

BACKGROUND OF INVENTION

The invention relates to a complete knee joint prosthesis intended to be implanted with ablation of the posterior cruciate ligament.

Such a prosthesis, known as a postero-stabilized prosthesis, generally consists of an element which is anchored in the end of the femur and has a shield which reproduces the femoral condyles and the trochlea of the natural joint, an element which is anchored in the end of the tibia and has an essentially plane upper wall perpendicular to the longitudinal axis of the tibia, and an intermediate plate which provides for the sliding of these two elements in relation to one another.

The intermediate plate comprises, on the side of the femoral element, two lateral glenoid cavities which receive the femoral condyles and, on the side of the tibial element, an essentially plane surface which comes to rest on the upper wall of the tibial element.

The plate also comprises a cam-shaped stud intended to be engaged in the trochlea of the femoral element, and the femoral element comprises a transverse intercondylar bar intended to come into abutment against the stud. This coming into abutment prevents posterior subluxation of the tibia, replacing the posterior cruciate ligament which has been removed.

The femoral and tibial elements are in general made of metal, while the intermediate plate is made of a material which favours sliding, such as high-density polyethylene.

During the movements of the joint, the femoral and tibial elements repeatedly exert great forces on the intermediate plate, which are applied in an unbalanced manner to a greater or lesser degree. In the long term, these forces cause wear and flow of the polyethylene plate, resulting in imbalance of the joint and abnormal stresses of the ligaments, and which may lead to loosening of the bone elements. This problem arises all the more because wear and flow increase as the femoral and tibial elements develop play in relation to the plate.

Furthermore, the contact between the stud of the plate and the intercondylar bar of the femoral element occurs relatively violently, in the middle of flexion, and takes place over a limited surface area, which contributes to wear of the plate and risks loosening of the elements.

These prostheses also suffer from problems of femoropatellar alignment, of limited mobility during flexion and of the existence of stresses during rotation which expose the prosthetic elements to loosening.

Prostheses exist, in which the plate is mounted pivotably in relation to the tibial element.

This mobility of the plate makes it possible to limit wear and flow of plastic plate, as well as limit the problems of femoropatellar alignment, limited mobility during flexion, and the existence of stresses during rotation without, however, eliminating them.

The aim of the present invention is to remedy this fundamental disadvantage of knee prostheses by providing a prosthesis which leads to minimal wear of the intermediate plate in the long term while retaining a mobility of the femoral and tibial elements which correspond to that of the natural joint.

SUMMARY OF THE INVENTION

The prosthesis to which the invention relates comprises, in a manner known per se, an element which is anchored in the end of the femur and reproduces the femoral condyles, an element which is anchored in the end of the tibia and has an essentially plane upper wall perpendicular to the longitudinal axis of the tibia, and an intermediate plate which provides for the sliding of these two elements in relation to one another, the plate being capable of pivoting in relation to the tibial element.

According to the invention, the following apply in combination:

the prosthetic condyles of the femoral element have a curvature in the shape of a circular arc in their rear part, and the femoral element has, between these condyles, a convex cylindrical wall which has an axis which coincides with the axis of the circular area in which the rear parts of the condyles lie;

the glenoid cavities of the intermediate plate have rear parts in the shape of a circular arc which have essentially the same radius, play excepted, as the rear parts of the condyles and an axis which coincides with that of the circle in which these same rear parts lie, while the intermediate plate comprises a central projecting rib in which a concave bearing surface in the shape of a circular arc is arranged, which has essentially the same radius, play excepted, as the convex cylindrical wall of the femoral element and has an axis which coincides with that of this wall, and the intermediate plate or the tibial element has a cylindrical pin forming a pivot, while the tibial element or, respectively, the intermediate plate comprises a cavity of a section which is greater than the cross section of this pin, the cavity being intended to receive the pin with the possibility of multidirectional movement.

When the femoral element is positioned above the intermediate plate, the condyles engage closely in the glenoid cavities, and the convex cylindrical wall of the femoral element comes closely into contact with the concave intercondylar bearing surface of the intermediate plate.

The convex wall and the concave bearing surface actually constitute a "third condyle" which makes possible not only postero-stabilization of the prosthetic joint but also perfect guidance of the femoral element on the intermediate plate, about a distinct transverse axis and according to a smooth flexion movement, as well as the preservation of a large contact surface area whatever the degree of flexion of the joint.

The pin and cavity of the tibial element and intermediate plate make possible multidirectional movement of the plate in relation to the tibial element, so that the plate can follow the anteroposterior and lateral movements of the femur in relation to the tibia and remains permanently in close contact with the femoral element. In fact, the high degree of femorotibial congruence renders any rotation between the femoral element and the intermediate plate impossible. This rotation is permitted without limit, however, between the intermediate plate and the tibial element.

Thus, in the prosthesis according to the invention, the contact surfaces of the femoral element and of the intermediate plate perform no relative anteroposterior or lateral translation movement, nor any pivoting movement about a vertical axis. Rather the contact so only a pivoting movement about a distinct transverse axis.

The result is that the risks of wear and flow of the intermediate plate, as well as the risks of loosening of the bone elements, are greatly reduced in relation to existing prostheses.

Furthermore, the large contact surface area between the femoral element and the intermediate plate allows good distribution of stresses, which contributes to limiting of wear.

The coefficient of friction of the intermediate plate on the tibial element is reduced to the greatest possible extent by polishing the upper face of the tibial element. The contact surface areas are large, which also allows the wear of the plate to be reduced.

The multidirectional movement of the intermediate plate, and therefore the self-positioning or self-centring of this plate in relation to the tibial element, makes it possible to limit the anteroposterior or mediolateral stresses during rotation, to which the intermediate plate is subjected. It also has the advantages indicated above.

On a highly congruent prosthesis, the internal lateral ligament tightens during flexion and prevents complete flexion. The mobility during rotation and the self-centring of the plate make it possible release the lateral ligamentous tensions and therefore to increase the possibility of complete flexion of the joint.

The anteroposterior mobility makes it possible to restore a rolling-sliding movement to the prosthesis, that is to say a pure sliding movement at the femoral element/intermediate plate interface and a rolling movement of the femur in relation to the tibia, limited to a few millimeters. During flexion, the intermediate plate advances until the pin comes into abutment against the wall delimiting the rear part of the cavity. Posterior stabilization is then provided for by the third condyle.

The lateral translation in turn makes it possible to compensate for a mediolateral centering error of the femoral or tibial element.

Advantageously, the central rib of the intermediate plate has a constant width, and the femoral element comprises an intercondylar cage which contains said concave bearing surface and comes to cover the rib without lateral play.

The lateral walls of this cage and of this rib constitute means of lateral retention of the femoral element in relation to the intermediate plate, preventing any lateral displacement which might cause wear.

Preferably, the cavity receiving the pin has an essentially oval shape, the length of which is oriented in the anteroposterior direction. This shape of the cavity allows an anteroposterior movement which is greater than the lateral movement, and makes it possible to reproduce the limited natural play of the femur in relation to the tibia.

Advantageously, the front parts of the condyles of the femoral element and the front parts of the glenoid cavities of the intermediate plate are congruent.

When the joint is extended, these front parts further increase the contact surface area of the femoral element and of the intermediate plate. The load exerted on the joint is thus distributed over a particularly large surface area, which also contributes to limiting the wear of the plate.

According to another advantageous characteristic, the upper face of the tibial element and the lower face of the intermediate plate are inclined by roughly 5° towards the rear to limit the risks of frontal lifting of the intermediate plate when the joint is at maximum flexion.

The prosthesis according to the invention may also comprise a patellar implant in the shape of a dome which comes into congruent contact with the prosthetic trochlea arranged in the front face of the femoral element, in the various flexion sectors of the joint.

In the event of incorrect rotational positioning of the tibial element, the rotation of the femur realigns the femoral and tibial elements, and re-centers the patella. The external subluxation of the patella is therefore prevented. During flexion, the lateral tensions exerted on the extensor apparatus are balanced by the adaptation of the position of the intermediate plate.

For the purpose of clear understanding, the invention is again described below with reference to the appended diagrammatic drawing showing, by way of non-limiting example, a preferred embodiment of the complete knee joint prosthesis to which it relates.

BRIEF DESCRIPTION OF THE DRAWINGS

FIG. 1 is an exploded perspective view of the various elements the prosthesis comprises;

FIG. 2 is a perspective view, from another angle, of its femoral element;

FIG. 3 is a view of the prosthesis in section along the line III—III in FIG. 4, and FIG. 4 is a view in section along the line IV—IV in FIG. 3.

DETAILED DESCRIPTION OF THE INVENTION

The figures show from different angles a femoral element 1, a tibial element 2 and an intermediate plate 3 of a knee joint prosthesis intended to be implanted with ablation of the posterior cruciate ligament.

The femoral element 1 is made of metal and has the general shape of a shield 4.

Its external face has two prosthetic condyles 5 which reproduce the femoral condyles, an intermediate recessed part 6 which reproduces the front part of the trochlea of the natural joint, a central cavity 7 delimited by an intercondylar cage 8, and a convex cylindrical wall 9 occupying the rear part of the cage 8.

FIG. 3 shows in greater detail that the prosthetic condyles 5 have a curvature in the shape of a circular arc in their rear part 5a, and that the cylindrical wall 9 has an axis which coincides with the axis of the circle in which these rear parts 5a lie.

On its internal face, which is intended to come into contact with the bone, the femoral element 1 comprises means (not shown) for anchoring to the bone. Said means may be inter alia a medullary rod, anchoring pins or spikes, or a porous covering which favours osteo-integration, such as a covering of calcium hydroxyapatite.

The tibial element 2 is also made of metal.

It comprises an anchoring leg 15 intended to be engaged in the medullary canal of the bone, and an essentially plane upper wall 16 intended to receive the plate 3.

The leg 15 is integral with three fins 17 which form gussets for reinforcing its connection to the wall 16 and constitute walls for stabilizing the element 2 during rotation. In its lower part, this leg 15 has a tapped bore which allows the positioning by screwing of an end-piece 18, it being possible to use a number of end-pieces of different length according to the anchoring depth used.

The wall 16 has a central cylindrical pin 20 which projects perpendicularly to its upper face. As shown in FIG. 3, this wall 16, with this pin 20, are inclined by roughly 5° towards the rear in relation to the axis of the leg 15.

The intermediate plate 3 is made of a material which favours sliding, such as high-density polyethylene.

It comprises, on the side of the femoral element 1, two lateral glenoid cavities 25 which receive the condyles 5, and, on the prosthetic side of the tibial element 2, an essentially plane surface which is inclined by 5° towards the rear so as to come to rest on the wall 16.

As shown in broken lines in FIG. 3, the glenoid cavities 25 have rear parts 25a in the shape of a circular arc, which have essentially the same radius, play excepted, as the rear parts 5a of the prosthetic condyles 5 and have an axis which coincides with that of rear parts.

The intermediate plate 3 also comprises a central projecting rib 30, in the rear face of which a concave bearing surface 31 in the shape of a circular arc is arranged. This bearing surface has the same radius, play excepted, as the cylindrical wall 9 and has an axis which coincides with that of the cylindrical wall 9.

In front of the wall 9, the cylindrical central project rib 30 has a slightly rounded front face 32, and the wall 33 of the femoral element delimiting the bottom of the cavity 7 has a corresponding shape, this wall 33 being intended to come to rest against the front face 32 when the joint is extended.

Furthermore, as can be seen in FIG. 4, the central projecting rib 30 has a constant width which corresponds, play excepted, to the width of the cavity 7, so that the intercondylar cage 8 comes to cover the rib 30 without lateral play.

In its lower face, the intermediate plate 3 comprises a cavity 35 of essentially oval shape, the length of which is oriented in the anteroposterior direction of the prosthesis. This cavity 35 has a section which is greater than the cross section of the pin 20 and which can receive the latter with the possibility of multidirectional movement.

FIGS. 3 and 4 show that the prosthetic condyles 5 engage closely in the glenoid cavities 25 and that the convex cylindrical wall 9 comes closely into contact with the concave bearing surface 31 when the femoral element 1 is positioned above the intermediate plate 3.

The prosthetic condyles 5 and convex cylindrical wall 9 can pivot in relation to the glenoid cavities 25 and the concave bearing surface 31, respectively. The concave cylindrical wall 9 and the concave bearing surface 31 actually constitute a "third prosthetic condyle", allowing posterostabilization of the joint and perfect guidance of the femoral element 1 on the intermediate plate 3 occurring about a distinct transverse axis and according to a smooth flexion movement, as allowing well as the preservation of a large contact surface area whatever the degree of flexion of the joint.

FIG. 3 also shows that the front parts of the prosthetic condyles 5 and of the glenoid cavities 25 are congruent. When the joint is extended, the front of the prosthetic condyles 5 and the respective glenoid cavities 25, as well as the front face 32 and the face 33, further increase the contact surface area of the femoral element 1 and the intermediate plate 3. The load exerted on the joint is thus distributed over a particularly large surface area.

The lateral walls of intercondylar cage 8 and of the central projecting rib 30 constitute a means of lateral retention of the femoral element 1 in relation to the intermediate plate 3.

The pin 20 and the cavity 35 allow multidirectional movement of the intermediate plate 3 in relation to the tibial element 2, so that the intermediate plate 3 can follow the anteroposterior and lateral movements of the femur in relation to the tibia yet remain permanently in close contact with the femoral element 1.

The inclination towards the rear of the upper wall 16 and of the lower surface of the intermediate plate 3 to limits the risks of frontal lifting of the plate 3 when the intermediate joint is at maximum flexion.

Thus, in the prosthesis according to the invention, the contact surfaces of the femoral element 1 and of the intermediate plate 3 perform no relative anteroposterior or lateral translation movement and no pivoting movement about a vertical axis but only a pivoting movement about a distinct transverse axis.

The result is that the risks of wear and flow of the intermediate plate 3, as well as the risks of loosening of the bone elements i.e., femoral element 1 and tibial element 2 are greatly reduced in relation to existing prostheses.

Furthermore, the large contact surface area between the femoral element 1 and the intermediate plate 3 allows good distribution of stresses, which contributes to limiting the wear thereof.

It is clear that the invention is not limited to the embodiment described above by way of example and that, on the contrary, it embraces all variant embodiments. Thus, the prosthesis may, in particular, comprise a patellar implant in the shape of a dome which comes into congruent contact with the prosthetic trochlea i.e., the intermediate recess 6 in the various flexion sectors of the joint.

What is claimed is:

1. A complete knee joint prosthesis comprising:
    a femoral element which is anchored in the end of the femur and provides prosthetic condyles having front and rear parts that reproduce the femoral condyles;
    a tibial element which is anchored in the end of the tibia and has an essentially plane upper wall perpendicular to the longitudinal axis of the tibia; and
    an intermediate plate which provides for the sliding of the femoral and tibial elements in relation to one another, the intermediate plate being capable of pivoting in relation to the tibial element,
    wherein the prosthetic condyles of the femoral element have rear parts with a curvature in the shape of a circular arc, and the femoral element has, between the prosthetic condyles, a convex cylindrical wall having an axis that coincides with the axis of the curvature in which the rear parts of the prosthetic condyles lie;
    the prosthetic condyles being received in glenoid cavities in an upper surface of the intermediate plate, the glenoid cavities having rear parts in the shape of a circular arc which have essentially the same radius, play excepted, as the rear parts of the prosthetic condyles and an axis that coincides with that of the curvature in which the prosthetic condyles' rear parts lie, the intermediate plate further comprising a central projecting rib in which a concave bearing surface in the shape of a circular arc is arranged, which has essentially the same radius, play excepted, for congruously receiving the convex cylindrical wall of the femoral element and has an axis which coincides with that of the convex cylindrical wall, and
    the intermediate plate or the tibial element having a cylindrical pin forming a pivot, while the tibial element or, respectively, the intermediate plate comprises a cavity, a section which is greater than the cross section of the pin, the cavity being intended to receive the pin with the possibility of multidirectional movement.

2. The knee prosthesis according to claim 1, wherein the central rib of the intermediate plate has a constant width, and the femoral element comprises an intercondylar cage which contains a concave bearing surface to cover the central rib without lateral play.

3. The knee prosthesis according to claim 1, wherein the cavity receiving the pin has an essentially oval shape, the length of which is oriented in the anteroposterior direction.

4. The knee prosthesis according to claim 1, wherein the front parts of the condyles and the glenoid cavities are congruent.

5. The knee prosthesis according to claim 1, wherein the central rib has a slightly rounded front face, and the femoral element has a wall of corresponding shape, the wall being intended to come to rest against the central rib's front face when the joint is extended.

6. The knee prosthesis according to claim 1, wherein the tibial element and of the intermediate plate are opposedly mated and inclined by roughly 5° towards the rear.

7. The knee prosthesis of claim 2, wherein the cavity for receiving the pin has an essentially oval shape, the length of which is oriented in the anteroposterior direction.

8. The knee prosthesis of claim 2, wherein the front parts of the prosthetic condyles are congruent with the glenoid cavities.

9. The knee prosthesis of claim 3, wherein the front parts of the prosthetic condyles are congruent with the glenoid cavities.

10. The knee prosthesis according to claim 8, wherein the central rib has a slightly rounded front face and the femoral element has a wall of corresponding shape, the wall being intended to rest against the central rib's front face when the joint is extended.

11. The knee prosthesis according to claim 9, wherein the central rib has a slightly rounded front face and the femoral element has a wall of corresponding shape, the wall being intended to rest against the central rib's front face when the joint is extended.

12. The knee prosthesis according to claim 4, wherein the central rib has a slightly rounded front face and the femoral element has a wall of corresponding shape, the wall being intended to rest against the central rib's front face when the joint is extended.

13. The knee prosthesis of claim 10, wherein the tibial element and the intermediate plate are opposedly mated and inclined by roughly 5° towards the rear.

14. The knee prosthesis of claim 11, wherein the tibial element and the intermediate plate are opposedly mated and inclined by roughly 5° towards the rear.

15. The knee prosthesis of claim 12, wherein the tibial element and the intermediate plate are opposedly mated and inclined by roughly 5° towards the rear.

16. The knee prosthesis of claim 5, wherein the tibial element and the intermediate plate are opposedly mated and inclined by roughly 5° towards the rear.

* * * * *